United States Patent [19]

Roling

[11] Patent Number: 5,221,764
[45] Date of Patent: Jun. 22, 1993

[54] METHODS AND COMPOSITIONS FOR INHIBITING ACRYLIC ACID POLYMERIZATION

[75] Inventor: Paul V. Roling, Spring, Tex.

[73] Assignee: Betz Laboratories, Inc., Trevose, Pa.

[21] Appl. No.: 837,519

[22] Filed: Feb. 18, 1992

[51] Int. Cl.$^5$ .............................................. C07C 69/52
[52] U.S. Cl. ...................................................... 560/205
[58] Field of Search ........................................ 560/205

[56] References Cited

U.S. PATENT DOCUMENTS

| | | | |
|---|---|---|---|
| 3,674,651 | 7/1972 | Otsuki et al. | 203/8 |
| 4,507,495 | 3/1985 | Dougherty et al. | 560/205 |
| 4,542,231 | 9/1985 | Dougherty et al. | 560/4 |
| 4,638,079 | 1/1987 | Inskip et al. | 560/4 |
| 4,814,493 | 3/1989 | Dougherty et al. | 560/205 |
| 4,912,247 | 3/1990 | Roling | 558/306 |

Primary Examiner—Paul J. Killos
Attorney, Agent, or Firm—Alexander D. Ricci; Philip H. Von Neida

[57] ABSTRACT

Methods and compositions are provided for inhibiting the polymerization of acrylic acid monomers during elevated temperature processing thereof or during storage or shipment of acrylic acid product. The compositions comprise a combination of a cerium source compound and an aromatic amine compound. The methods comprise adding from about 1 to about 10,000 parts per million to the particular acrylic acid containing medium for which such polymerization inhibition is desired, per million parts of the acrylic acid medium.

14 Claims, No Drawings

METHODS AND COMPOSITIONS FOR INHIBITING ACRYLIC ACID POLYMERIZATION

FIELD OF THE INVENTION

The present invention pertains to methods and compositions for inhibiting the undesired polymerization of acrylic acid monomers during processes such as monomer preparation, and purification, and during storage and shipment of products containing such monomers.

BACKGROUND OF THE INVENTION

Polymerizable acrylic acids undesirably polymerize during various stages of the manufacturing, processing, handling, storage and use thereof. One especially troublesome problem is the polymerization of acrylic acid monomer in the purification stages of monomer production. It is well known that the monomer readily polymerize and that such polymerization increases with concurrent temperature increases.

Polymers are generally formed by free radical chain reactions. These reactions, shown below, consist of two phases, an initiation phase and a propagation phase. In Reaction 1, the chain initiation reaction, a free radical represented by R•, is formed (the symbol R• can be any hydrocarbon). These free radicals, which have an odd electron, act as chain carriers. During chain propagation, additional free radicals are formed and the hydrocarbon molecules (R) grow larger and larger (see Reaction 2c), forming the unwanted polymers which accumulate on heat transfer surfaces.

Chain reactions can be triggered in several ways. In Reaction 1, heat starts the chain. Example: When a reactive molecule such as an olefin or a diolefin is heated, a free radical is produced. Another way a chain reaction starts is shown in Reaction 3. Metal ions initiate free radical formation here. Accelerating polymerization by oxygen and metals can be seen by reviewing Reactions 2 and 3.

As polymers form, more polymers begin to adhere to the heat transfer surfaces. This adherence results in dehydrogenation of the hydrocarbon and eventually the polymer is converted to coke.

1. Chain Initiation

R—H→R•+H•

2. Chain Propagation
 a. R•+O$_2$→R—O—O•
 b. R—O—O•+R'—H→R'•+R—O—O—H
 c. R'•+C=C→R'—C—C•→Polymer
3. Chain Initiation
 a. Me$^{++}$+RH→Me$^+$+R•+H$^+$
 b. Me$^{++}$+R—O—O—H→Me$^+$+R—O—O•+H$^+$
4. Chain Termination
 a. R•+R•→R—R'
 b. R•+R—O—O•→R—O—O—R Research indicates that even very small amounts of oxygen can cause or accelerate polymerization. Accordingly, to inhibit this insidious fouling problem, it is highly desirable to provide a polyfunctional process antifoulant which can, among other functions, inhibit oxygen based polymerization initiation. This antioxidant function serves as a "chain-stopper" by forming inert molecules with the free radicals similar to the chain termination as indiciated in reactions 4a and 4b.

Common industrial methods for producing acrylic acids include a variety of purification processes, including distillation to remove impurities. Unfortunately, purification operations carried out at elevated temperatures result in an increased rate of undesired polymerization. Polymerization, such as thermal polymerization, during the monomer purification process, results not only in loss of desired monomer end-product, but also in loss of production efficiency caused by polymer formation or agglomeration on process equipment. In heat requiring operations, such agglomeration adversely affects heat transfer efficiency.

SUMMARY OF THE INVENTION

The present invention provides for compositions and methods for inhibiting acrylic acid monomer polymerization comprising adding to the monomer an effective amount for the purpose of an aromatic amine compound and a cerium source compound.

DESCRIPTION OF THE RELATED ART

U.S. Pat. No. 4,542,231, Dougherty et al., September 1985 teaches compositions of cerium compounds, such as acrylic acid. Catechol and hydroquinone are representative of the phenolic type inhibitors.

U.S. Pat. No. 4,507,495, Dougherty et al., March 1985 discloses processes for producing ethyl acrylate by reacting ethylene and acrylic acid in the presence of sulfuric acid. Cerium and manganese containing compounds are added to the reaction mixture to improve the efficiency of the reaction.

U.S. Pat. No. 4,912,247, Roling, March 1990 teaches methods and compositions for inhibiting acrylate monomer polymerization. The composition comprises a combination of a Mannich reaction product and either phenylenediamine or phenothiazine or their derivatives.

A variety of compositions and methods have been proposed for inhibiting uncontrolled polymerization of (meth)acrylic acrylic acid and esters. Known inhibitors include phenothiazine, methylene blue, hydroquinone, hydroquinone methyl ether (MEHQ) and sundry mangahese containing compounds.

Of somewhat lesser importance is U.S. Pat. No. 4,638,079 Inskip et al. which discloses processes for inhibiting polymerization of polymerizable ethylenically unsaturated monomers such as hydrocarbons, acids and esters wherein a cobalt (III), nickel (II), or manganese (II) complex of N-nitrosophenylhydroxylamine is utilized. In a preferred embodiment of the U.S. Pat. No. 4,638,079 disclosure, polymerization of an acrylic acid or acrylate ester is inhibited.

U.S. Pat. No. 3,674,651 Otsuki et al discloses a process for inhibiting the polymerization of acrylic acid using a combination of diphenylamine or its derivatives and an oxygen containing gas. This combination can also employ benzoquinone and/or hydroquinone monomethyl ether.

As seen from the related art, the combination of cerium source compound and aromatic amine surprisingly inhibit the polymerization reactions of acrylic acid and (meth)acrylic acid better than the sum of the individual components.

DETAILED DESCRIPTION OF THE INVENTION

In accordance with the present invention, methods and compositions are provided for inhibiting the polymerization of acrylic acid monomers comprising adding to said monomer an effective amount for the purpose of a combination of a cerium containing compound and an aromatic amine compound. The phrase "acrylic acid monomers" as used herein is intended to include acrylic acid, (meth)acrylic acid, crotonic acid, and isocrotonic acid.

Although it is not important as to the form in which the cerium is added to the acrylic acid monomers, examples of cerium source compounds which can be used include cerium in the cerous or ceric state with anions of nitrate, ammonium nitrate, acetate, propionate, butyrate, neopentoate, octoate, laurate, neodecanoate, stearate, naphthenate, oxalate, maleate, benzoate, acrylate, salicylate, versalate, terephthalate, carbonate, hydroxide, sulfate, fluoride, organosulfonate, acetylacetonate, beta-diketones, oxide (water based or hydrocarbon based suspension), ortho-phosphate, or combinations of the above. TX-3024D available from Sybron is a commercially available cerium source.

The aromatic amine compounds can include phenylenediamine compounds and their derivatives and phenothiazine compounds and their derivatives.

The phenylenediamine component of the inhibitor mixtures of this invention include phenylenediamine and derivatives thereof having at least one N-H group. It is thought that o-phenylenediamine or derivatives thereof having at least one N-H group are suitable in accordance with the instant invention. However, the preferred phenylenediamine is p-phenylenediamine having the formula

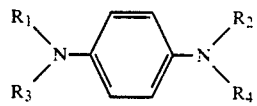

wherein $R_1$, $R_2$, $R_3$, and $R_4$ are the same or different and are hydrogen, alkyl, aryl, alkaryl, aralkyl groups with the proviso that at least one of $R_1$, $R_2$, $R_3$, or $R_4$ is hydrogen, more preferably the alkyl, aryl, alkaryl, and aralkyl groups have one to about twenty carbon atoms The alkyl, aryl, alkaryl, and aralkyl groups may be straight or branched-chain groups. Exemplary p-phenylenediamines include p-phenylenediamine wherein $R_1$, $R_2$, $R_3$, and $R_4$ are hydrogen; N-phenyl-N'-alkyl-p-phenylenediamines such as, N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-n-butyl-p-phenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexl-p-phenylenediamine, N-phenyl-N'-(l-methylhexl)-p-phenylenediamine, N-phenyl-N'-(1,3-dimethylbutyl)-p-phenylenediamine, N-phenyl-N'-(1,4-dimethylpentyl)-p-phenylenediamine; N-phenyl-N',N'-dialkyl-p-phenylenediamines, such as N-phenyl-N',N'-dimethyl-p-phenylenediamine, N-phenyl-N',N'-diethyl-p-phenylenediamine, N-phenyl-N',N'-di-n-butyl-p-phenylenediamine, N-phenyl-N',N'-di-sec-butyl-p-phenylenediamine, N-phenyl-N'-methyl-N'-ethyl-p-phenylenediamine; N,N-dialkyl-p-phenylenediamines such as N,N-dimethyl-p-phenylenediamine and N,N'-diethyl-p-phenylenediamine; N,N'-dialkyl-p-phenylenediamines such as N,N'-di-isopropyl-p-phenylenediamine; N,N'-diaryl-p-phenylenediamines such as N,N'-diphenyl-p-phenylenediamine; N,N,N'-trialkyl-p-phenylenediamines such as N,N,N'-trimethyl-p-phenylenediamine, N,N,N'-triethyl-p-phenylenediamine. Preferably, the p-phenylenediamine is selected from the group consisting of N-phenyl-N'-(1,3-dimethylbutyl)-p-phenylenediamine and N-phenyl-N'-(1,3-dimethylpentyl)-p-phenylenediamine.

The phenothiazine compounds useful in this invention have the formula

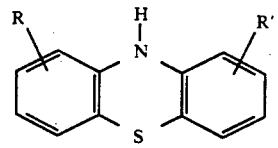

wherein R and R' are the same or different and are hydrogen, alkyl, aryl, alkaryl or aralkyl group.

Examples of suitable phenothiazine derivatives include: phenothiazine, 1-methylphenothiazine, 2-methylphenothiazine, 3-methylphenothiazine, 4-methylphenothiazine, 1,3-dimethylphenothiazine, 1,4-dimethylphenothiazine, 1,6-dimethylphenothiazine, 2-ethylphenothiazine, 3,7-dioctylphenothiazine, and 1-benzylphenothiazine.

The total amount of combined treatment used in the methods of the present invention is that amount which is sufficient to effect inhibition of polymerization and will, of course, vary according to the conditions under which the monomer is synthesized, processed and/or stored. At higher processing or storage temperatures, larger amounts of the polymerization inhibiting treatment are generally required.

Preferably, the total amount of the combined treatment is from about 2 part per million to about 10,000 parts per million parts combined treatment based on the weight of the acrylic acid monomer. Most preferably, the total amount of the combined treatment is from about 5 parts per million to about 1000 parts per million based on the weight of the acrylic acid monomer.

The weight ratios of cerium compound (as cerium) to the aromatic amine compounds are preferably in the range of about 0.05:1 to about 2.5:1. Most preferably, the weight ratio is about 0.1:1 to about 1:1.

The methods of the present invention can control the fouling of processing equipment, such as the equipment used in separation and purification processes of acrylic acid monomer, which is due to or caused by the polymerization of the monomer. The instant invention may be used as both a process inhibitor, which is employed during preparation and processing of the acrylic acid monomer at elevated temperature, and as a product inhibitor, which is combined with the acrylic acid in order to inhibit polymerization of the monomer during storage and handling.

The combined polymerization treatment can be added to the acrylic acid monomer by any conventional method. The components can be added separately or as a combination containing both components. It is clearly preferred to add the composition as a single treatment composition containing both the cerium containing compound and the aromatic amine compound.

Accordingly, it is therefore possible to produce a more effective acrylic acid polymerization inhibition treatment than is obtainable by the use of either individual ingredient alone when measured at comparable treatment levels. Because of the enhanced polymerization activity of the combination, the concentration of each of the ingredients may be lowered and the total quantity of the polymerization inhibitor required for an effective treatment at elevated temperatures may be reduced. This factor is especially important in monomer purification procedures where the obvious goal of the process is to provide high level monomer purity.

The composition may be added as either a dispersion or as a solution using a suitable liquid carrier dispersing medium or solvent which is compatible with the acrylic acid. Preferably, a solution is provided and the solvent is an organic solvent such as xylene (a commercial mixture of o, m and p isomers) or heavy aromatic naphtha.

The preferred inventive embodiments employ an organic salt of cerium and either a para-phenylenediamine or phenothiazine in combination in a 0.5:1 weight ratio of components dissolved in xylene. Optimal dosage rates for the composition are on the order of from about 5 parts per million to about 1000 parts per million of the combined cerium containing compound, as cerium and aromatic amine compound per one million parts of the acrylic acid monomer for which polymerization inhibition is desired.

The data set forth below were developed and demonstrate the unexpected results occasioned by use of the invention. The following examples are included as being illustrations of the invention and should not be construed as limiting the scope thereof.

EXAMPLES

N-phenyl-N'-(1,4-dimethylpentyl)-p-phenylenediamine (PDP) and phenothiazine (PTZ) were the aromatic amine compounds tested with the cerium containing compounds. Evaluation of the inhibitor combinations was carried out using acrylic acid, which was distilled under vacuum, with the portion distilling about 35° to 40° C./5 Torr being used, to remove the majority of hydroquinone methyl ether (MEHQ) inhibitor. Phenothiazine was added to the distillation flask to inhibit the distilling acrylic acid.

In a 17-ml test-tube was placed 5.0 ml of the distilled acrylic acid and the appropriate amount of inhibitor, either singly or in combination (in a 0.10 weight-/volume % solution in xylene). The tube was sealed with a tight-fitting septum cap and a 9-inch long, 4-mm diameter soft glass tube closed at the bottom and partly filled with mineral oil was inserted through the septum to the bottom of the test-tube. A thermocouple was then placed in the 4-mm tube and the entire set-up was then placed in an oil bath kept at a temperature of about 224° F. The temperature of the sample was monitored on a datalogger with the time for the exothermic polymerization reaction being recorded. Exotherms for samples were sharp and large, with peak temperatures being about 400° F.

All examples were conducted with air present in the test-tube. Generally, from five to ten tubes were run at a time in the oil bath. Exotherm times varied from set to set, possibly depending on the efficiency of the distillation for removing the MEHQ. The longer the time to exotherm, the better the polymerization inhibition. The results of this testing is presented in Table I.

TABLE I

| Treatments | Dosage (ppm) | Run 1 | Run 2 | Run 3 | Run 4 | Run 5 | Run 6 |
|---|---|---|---|---|---|---|---|
| Blank | 0 | 21 | 24 | 17 | 21 | 21 | 20 |
| Ce | 1 | | | | 131 | | |
| Ce | 2 | | | | 95 | 108 | 222 |
| Ce | 3 | 101 | 64 | 198 | | | |
| Ce | 6 | 105 | | | | | |
| PDP | 1 | | | | 21 | | |
| PDP | 2 | | | | 20 | 20 | |
| PDP | 6 | 17 | 19 | 20 | | | |
| Ce-PDP | 1-1 | | | | 129 | | |
| Ce-PDP | 1-2 | | | | 161 | | 183 |
| Ce-PDP | 2-1 | | | | 139 | | 234 |
| Ce-PDP | 2-2 | | | | 257 | 173 | 321 |
| Ce-PDP | 3-3 | 280 | | | | | |
| Ce-PDP | 3-6 | 360 | 521 | 1311 | | | |
| Ce-PDP | 6-3 | 233 | | | | | |
| Ce-PDP | 6-6 | 1245 | 321 | 3543 | | | |
| PTZ | 2 | | | | 17 | 23 | 24 |
| PTZ | 6 | 26 | | | | | |
| Ce-PTZ | 6-6 | 2521 | | | | | |

Ce = short-chained carboxylic acid salt of cerium
PDP = N-phenyl-N'-(1,4-dimethylpentyl)-p-phenylenediamine
PTZ = phenothiazine In this example, various amounts of cerium containing compound, phenylenediamine and phenothiazine were added to the acrylic acid. In the controls, where no inhibitor was employed, the acrylic acid polymerized in 17 to 24 minutes as evidenced by the exotherms. The addition of phenylenediamine alone and phenothiazine alone did not significantly increase inhibition time versus the controls. However, the combinations of cerium containing compounds with the two aromatic amine compounds showed enhanced efficacy over the sum of the individual components when the total part per million level of the two components was greater than about 2.

While this invention has been described with respect to particular embodiment thereof, it is apparent that numerous other forms and modifications of this invention will be obvious to those skilled in the art. The appended claims and this invention generally should be construed to cover all such obvious forms and modifications which are within the true spirit and scope of the present invention.

What I claim is:

1. A method for inhibiting acrylic acid monomer polymerization comprising adding to the monomer an effective inhibiting amount of (a) a cerium source compound and (b) a phenylenediamine compound.

2. The method as claimed in claim 1 wherein said phenylenediamine compound has the structure

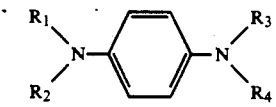

wherein $R_1$, $R_2$, $R_3$, and $R_4$ are the same or different and are hydrogen, alkyl, aryl, alkaryl or aralkyl, with the proviso that at least one of $R_1$, $R_2$, $R_3$, and $R_4$ is hydrogen.

3. The method as claimed in claim 2 wherein $R_1$, $R_2$, $R_3$, or $R_4$ each have from 1 to 20 carbon atoms except for at least one of $R_1$, $R_2$, $R_3$, or $R_4$ that is hydrogen.

4. The method as claimed in claim 1 wherein said phenylenediamine compound is N-phenyl-N'-(1,4-dimethylpentyl)-p-phenylenediamine.

5. The method as claimed in claim 1 wherein the weight ratio of (a):(b), wherein (a) is measured as cerium, is from about 0.05:1 to about 2.5:1.

6. The method as claimed in claim 1 wherein the amount of (a) and (b) added in combination to the acrylic acid monomer is from about 2 part per million to about 10,000 parts per million parts of the monomer.

7. The method as claimed in claim 6 wherein the amount of (a) and (b) added in combination to the acrylic acid monomer is from about 5 parts per million to about 1000 parts per million parts of the monomer.

8. Acrylic acid anti-polymerization comprising a liquid carrier and dispersed or dissolved therein (a) a cerium source compound and (b) a phenylenediamine compound.

9. The composition as claimed in claim 8 wherein said phenylenediamine compound has the structure

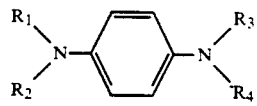

wherein $R_1$, $R_2$, $R_3$, and $R_4$ are the same or different and are hydrogen, alkyl, aryl, alkaryl, or aralkyl, with the proviso that at least one of $R_1$, $R_2$, $R_3$, or $R_4$ is hydrogen.

10. The composition as claimed in claim 9 wherein $R_1$, $R_2$, $R_3$, or $R_4$ each have from 1 to 20 carbon atoms except for at least one of $R_1$, $R_2$, $R_3$, or $R_4$ that is hydrogen.

11. The composition as claimed in claim 9 wherein said phenylenediamine compound is N-phenyl-N'-(1,4-dimethylpentyl)-p-phenylenediamine.

12. The composition as claimed in claim 8 wherein said liquid carrier comprises an organic solvent and wherein (a) and (b) are both dissolved in said solvent.

13. The composition as claimed in claim 12 wherien said organic solvent comprises xylene.

14. The composition as claimed in claim 8 further comprising acrylic acid monomer.

* * * * *